April 1, 1947. M. A. DAUERNHEIM Plant Pat. 733
AZALEA PLANT
Filed March 6, 1946
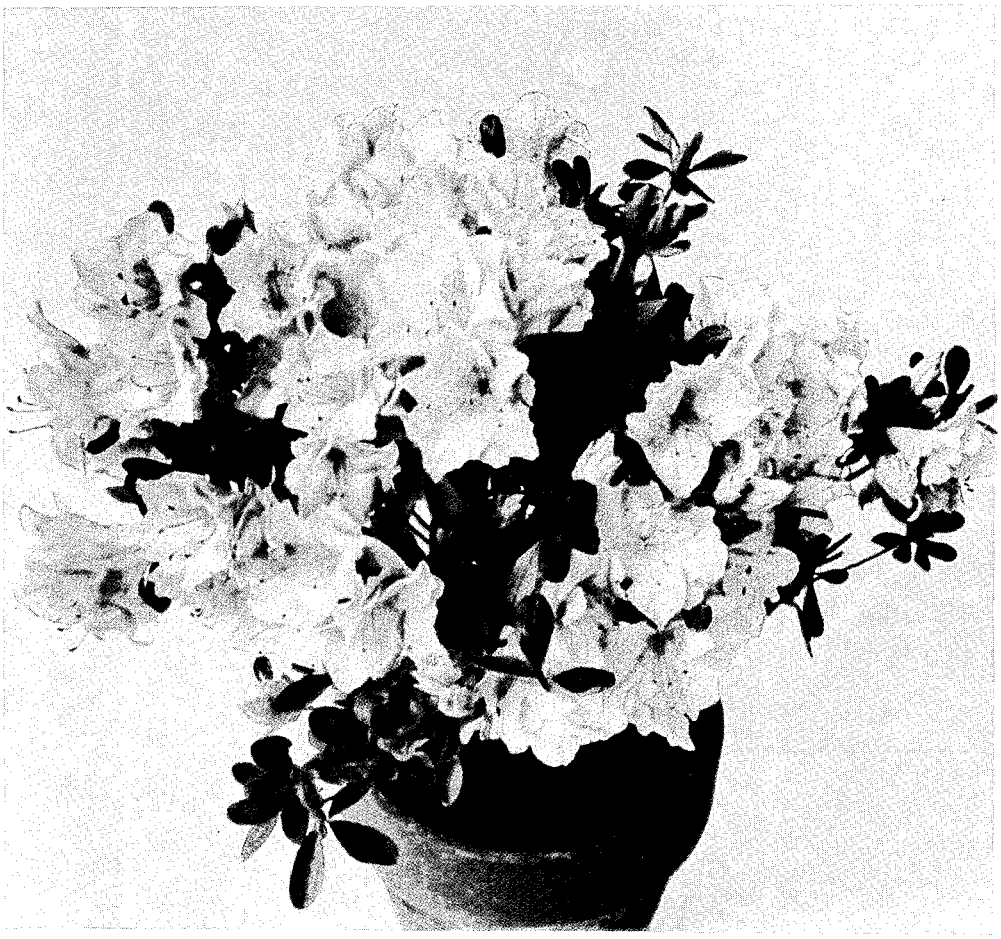
Inventor
M. A. Dauernheim
By Robert Robb
Attorney Patented Apr. 1, 1947

Plant Pat. 733

UNITED STATES PATENT OFFICE

733

AZALEA PLANT

Mel A. Dauernheim, Wantagh, N. Y., assignor to Dauernheim, Inc., Wantagh, N. Y., a corporation of New York Application March 6, 1946, Serial No. 652,269

1 Claim. (Cl. 47—60)

The present discovery relates to a new and distinct variety of azalea plant, originating as a sport of the well-known variety "Mme. Pericat."

This new azalea was discovered by me as a branch growing upon its parent plant among a group of "Mme. Pericats" and recognized as possessing important distinctions from this variety, as hereinafter more particularly pointed out.

"Mme. Pericat," the parent plant, is an excellent one for blooming from March 15th to May 15th. It is particularly good for late flowering as it resists heat exceptionally well and is an excellent keeper under warm conditions. The present sport variety has all the good characteristics of its parent, but is primarily distinctive for its unusual color of bloom, a color which is more popular than that if its parent for the average public taste.

The accompanying drawing shows a potted specimen of this new variety, showing the typical phlox pink coloring of the blossoms. As will be apparent, this coloring is evenly distributed, considerably deeper than that of the parent variety and more distinctive for this reason. By comparison with its parent variety, which it resembles more than any other variety, this new azalea will be found to be similar in habit of growth, form and size of flower. It is, however, one of the latest varieties to bloom of the Karume type.

Asexual reproduction of this new variety shows the foregoing characteristics come true to form and are established.

The following is a detailed description of the new variety, color terminology being in accord with the ordinary dictionary definition, except where indicated to be in accordance with the R. F. Wilson's Horticultural Colour Chart:

Propagation: Holds its distinguishing characteristics through succeeding propagations by cuttings.

Growth habit: Vigorous, but not quite as vigorous as parent plant, "Mme. Pericat." General habit of growth similar to "Mme. Pericat."

Rooting: Similar to "Mme. Pericat"; easy rooting.

Blooming habit: Blooms evenly as most all azalea varieties grown to flower at proper season.

Blooming season: As it is a semi-hardy variety it is not feasible to determine exactly when it would bloom naturally. This and similar varieties are carried through their dormancy with protection. Older plants (two-year and older) may be carried through winter in cold frames, and in this location bloom about May 10th–20th.

Suitability for forcing: Plants which are field grown during summer and potted anytime from fall on and properly storaged during dormancy, may be forced in good shape from March 20th to May 10th. Plants which are not grown during the summer and properly storaged during dormany may be forced in good shape as early as February 15th. This new variety is an excellent forcer for late blooming, as it is not affected as much by the heat as early flowering types.

Foliage:

*Size.*—Large for a Kurume type. Under conditions where these observations were made, the mature foliage of the strongest branches is from 1¼ to 1½ inches long. If plants are not pinched often and growth is straggly, foliage may be larger.

*Quantity.*—Normal.

*Color.*—*New foliage*—upper side—lighter that mature foliage; under side—lighter than mature foliage. *Old foliage*—upper side—Parsley Green, Plate 00962, page 193; under side—somewhat lighter than upper.

*Shape.*—Oval; occasionally pointed.

*Texture.*—Upper side—glossy but not smooth; under side—less glossy and rougher than upper side.

*Edge or margin.*—Smooth.

*Disease resistance.*—Good.

*Flower*

Locality where specimens described were grown: Wantagh, Long Island, New York.

Flowers borne: Bud sheaths contain from three flowers to large clusters of nine or more on strongest and tallest branches.

Quantity of bloom: Free and abundant under greenhouse conditions.

Continuity: One crop per season, unless plant is checked in some manner and unseasonable buds are formed.

Petalage: A hose-in-hose type, each layer of which is star-shaped. The size of the flowers are from 1½ to 2 inches in diameter.

*Color.*—Phlox Pink, Plate 625/1, page 77.
*Texture.*—Similar to "Mme. Pericat."
*Appearance.*—Inside—even distribution of color with a mottling of deeper spots, which do not detract from general mass effect. Outside—similar color to inside, except somewhat lighter toward the base.
*Shape.*—Each layer star-shaped with the points of the lower layer bisecting the points of the upper layer.

Bud: Pointed. Same color as open flower when almost open. The tips, particularly on smaller buds, may be a trifle lighter.

Reproductive organs:
*Stamens.*—Brown tips with light pink stems.
*Pollen.*—Light Green.
*Styles.*—Rose color. Just a trifle longer and thicker than the stamens.

I claim:

A new and distinct variety of azalea plant characterized as to novelty by its late blooming habit and unique pink coloring of the flowers, substantially as shown and described.

MEL A. DAUERNHEIM.